United States Patent [19]

Bernstein

[11] Patent Number: 5,063,060

[45] Date of Patent: Nov. 5, 1991

[54] COMPOSITIONS AND METHOD FOR TREATING PAINFUL, INFLAMMATORY OR ALLERGIC DISORDERS

[75] Inventor: Joel E. Bernstein, Deerfield, Ill.

[73] Assignee: Cisco Limited Partnership, Lincolnshire, Ill.

[21] Appl. No.: 452,476

[22] Filed: Dec. 19, 1989

[51] Int. Cl.$^5$ .................. A61K 9/02; A61K 9/20; A61K 1/48; A61K 31/16
[52] U.S. Cl. ............................... 424/422; 424/436; 424/451; 424/464; 424/195.1; 514/627; 514/887; 514/914; 514/967
[58] Field of Search ............... 424/422, 436, 451, 464, 424/195.1; 514/627, 887, 914, 937, 944, 967

[56] References Cited

U.S. PATENT DOCUMENTS

| | | | |
|---|---|---|---|
| 4,493,848 | 1/1985 | Lahann et al. | 514/627 |
| 4,536,404 | 8/1985 | Bernstein | 514/944 |
| 4,702,916 | 10/1987 | Geria | 514/944 |
| 4,812,446 | 3/1989 | Brand | 514/627 |

*Primary Examiner*—Thurman K. Page
*Assistant Examiner*—Amy Hulina
*Attorney, Agent, or Firm*—Jones, Day, Reavis & Pogue

[57] ABSTRACT

The invention relates to a method of treating painful, inflammatory or allergic disorders comprising treatment with an effective amount of a composition comprising cis-8-methyl-N-vanillyl-6-nonenamide. The invention also relates to compositions for use in the inventive method.

14 Claims, No Drawings

COMPOSITIONS AND METHOD FOR TREATING PAINFUL, INFLAMMATORY OR ALLERGIC DISORDERS

BACKGROUND OF THE INVENTION

Capsaicin (trans-8-methyl-N-vanillyl-6-nonenamide) is a compound derived from plants of the Solanacea family, commonly known as hot red peppers. Capsaicin has been utilized over the last two decades to study the neurophysiology and pharmacology of pain, as well as for the treatment of certain types of neuropathies and skin disorders. Such use is disclosed, for example, in U.S. Pat. No. 4,486,450, issued Dec. 4, 1984, and entitled "Method Of Treating Psoriatic Skil And Composition," and U.S. Pat. No. 4,536,404, issued Aug. 20, 1985, and entitled "Method And Composition For Treating Post-Herpetic Neuralgia;" both patents issued to the applicant herein.

While capsaicin is useful in treating painful neurological and other disorders, its utility has been limited by a troublesome adverse reaction which almost invariably accompanies its use. This reaction is a localized stinging and burning sensation, which can be quite severe, on application of capsaicin topically to skin or mucous membranes or on injection into tissues such as the dermis, the cerebrospinal canal or into blood vessels.

Attempts to reduce or eliminate this adverse effect have had only limited success, and include the incorporation of an anesthetic into the formulation. Since the stinging and burning have been thought to be directly linked to capsaicin's effects on neuropeptides in nerves, and these capsaicin effects on neuropeptides are thought to be crucial to capsaicin's efficacy in relieving pain, it has been considered impossible to significantly reduce the stinging and burning without greatly reducing or eliminating capsaicin's effectiveness.

When capsaicin is extracted from the pepper plant, such extracts contain a number of other compounds similar in structure to capsaicin, but with different properties. A number of these compounds, known as capsinoids, have been evaluated for their ability to deplete neuropeptides. None of these capsinoids has been found to be as effective as capsaicin in depleting the neuropeptides, and all of those known to have any measurable neuropeptide depleting activity also cause an uncomfortable degree of burning and stinging.

It is thus an object of the invention to provide methods of treating painful, inflammatory, or allergic disorders without the adverse stinging and burning associated with the use of capsaicin.

It is still another object of the invention to provide pharmaceutically acceptable compositions suitable for use in the inventive method.

In an attempt to discover a capsinoid which might be able to be more cheaply substituted for capsaicin in medicinal formulations, applicant has evaluated cis-8-methyl-N-vanillyl-6-nonenamide, a stereoisomer of capsaicin. The existence of this capsinoid in small quantities in pepper extracts has been known for some time. It has, however, always been believed that, like the other capsinoids, cis-8-methyl-N-vanillyl-6-nonenamide lacked significant neuropeptide depleting activity.

Applicant has discovered, quite surprisingly, that cis-8-methyl-N-vanillyl-6-nonenamide is much more potent as a depleter of neuropeptides from sensory nerves than is capsaicin. Even more surprisingly, applicant has discovered that cis-8-methyl-N-vanillyl-6-nonenamide produced such neuropeptide depletion without producing the extreme degree of burning or stinging produced by capsaicin. The invention therefore includes compositions of cis-8-methyl-N-vanillyl-6-nonenamide incorporated in topical formulations suitable for application to skin or mucous membranes, which compositions can produce in both man and animals pronounced analgesia without the pronounced irritant effects of capsaicin. The invention also includes compositions of cis-8-methyl-N-vanillyl-6-nonenamide incorporated into other medicinal formulations suitable for injection, oral ingestion, pulmonary inhalation, rectal administration or ophthalmic or nasal administration. When incorporated into such medicinal formulations, cis-8-methyl-N-vanillyl-6-nonenamide is substantially more potent than capsaicin and will produce less local irritation in the form of burning, stinging or vasodilitation than capsaicin. The invention also includes methods of using the inventive compositions to treat painful, inflammatory, or allergic disorders.

DETAILED DESCRIPTION OF THE PREFERRED EMBODIMENTS

In accordance with the invention, formulations are provided that incorporate cis-8-methyl-N-vanillyl-6-nonenamide into pharmaceutically acceptable vehicles suitable for use in man and animals. Such formulations include those for application to the skin, such as solutions, creams, ointments, gels, lotions, or pastes. Such formulation also include those for application to mucous membranes, including opthalmic and nasal solutions and suspensions, suppositories, and plasticized formulations suitable for oral and vaginal applications. Cis-8-methyl-N-vanillyl-6-nonenamide may also be formulated in sterile solutions or suspensions suitable for intradermal, subcutaneous, intramuscular, intravenous, or cerebrospinal injection. In each of the foregoing formulations, whether for application to the skin, application to the mucous membranes, or for injection, the cis-8-methyl-N-vanillyl-6-nonenamide may be present in the amount of about 0.001% to about 1.0% by weight, and preferably about 0.005% to about 0.25% by weight. The cis-8-methyl-N-vanillyl-6-nonenamide can be purchased from Eudora Research and Development Ltd., Sussex, United Kingdom.

Formulations within the scope of the invention also include those suitable for oral administration such as capsules, tablets, or liquid solutions or suspensions. In such formulations, the cis-8-methyl-N-vanillyl-6-nonenamide may be present in amounts of about 0.1–100.0 mg, and preferably about 0.5–50.0 mg, per tablet, capsule, or 5 ml dose of liquid solution or suspension.

Suitable pharmaceutical vehicles for the cis-8-methyl-N-vanillyl-6-nonenamide whether for topical application to skin or mucous membrane, injection, or oral administration, and methods of preparing such formulations as are within the scope of the invention, will be readily apparent to and understood by those skilled in the art.

The instant invention also comprises the method of applying, instilling, injecting, ingesting, or inhaling medicinal formulations containing cis-8-methyl-N-vanillyl-6-nonenamide in order to treat a wide range of painful and/or inflammatory disorders of man and animals such as neuropathies, skin disorders, arthritis, allergic disorders, and inflammatory bowel disorders.

The compositions of the instant invention and the methods of their use will be more readily comprehended from the following examples.

EXAMPLES

EXAMPLE 1

Cis-8-methyl-N-vanillyl-6-nonenamide was incorporated into a pharmacologically inert cream vehicle at a concentration of 0.025% and capsaicin was incorporated into the same cream vehicle at the identical concentration. The two creams were applied to 5 cm diameter patches on the forearms of 75 human volunteers under a randomized double-blind design. Each cream was applied 4 times over a 48 hour period and then the patients were examined. Stinging, burning and erythema were noted and rated for severity in each area. It was observed that while relatively frequent and severe local reactions were noted with capsaicin, the application of cis-8-methyl-N-vanillyl-6-nonenamide caused much less frequent, milder local reactions. Differences in both degree of stinging or burning and erythema noted between cis-8-methyl-N-vanillyl-6-nonenamide and capsaicin were statistically significant in favor of cis-8-methyl-N-vanillyl-6-nonenamide.

EXAMPLE 2

Male Sprague Dawley rats were prepared under halothane anesthesia with lumbar intrathecal catheters. After a 5-day period of recovery the rats received an intrathecal injection of either cis-8-methyl-N-vanillyl-6-nonenamide, capsaicin or a control vehicle and then nociception tested with a 49° C. hot plate. In this test performed 1, 3 and 7 days following treatment with cis-8-methyl-N-vanillyl-6-nonenamide, capsaicin, or control vehicle, the rats are placed on a surface maintained at 49° C. The anticipated endpoint is either a jump or a licking of the hindpaw. The latency to this response is measured. Failure to lick in 120 seconds is cause for termination of the test and assignment of that score. The results of this test showed that at doses of 1 and 10 ug, latencies of animals treated with cis-8-methyl-N-vanillyl-6-nonenamide were statistically significantly greater than those treated with capsaicin or the control vehicle.

EXAMPLE 3

The male Sprague Dawley rats of Example 2 were sacrificed 7 days following treatment, then decapitated, and the spinal cords rapidly removed by hydraulic pressure. Cords were frozen and then assayed for the neuropeptides substance P(SP) and Calcitonin Gene Related Peptide (CGRP). The injection of either cis-8-methyl-N-vanillyl-6-nonenamide or capsaicin resulted in dose dependent decreases in the levels of SP and CGRP in the dorsal but not ventral horns of the rat lumbosacral spinal cord. Cis-8-methyl-N-vanillyl-6-nonenamide was statistically significantly more potent than capsaicin in decreasing levels of SP. The two chemicals were equally effective in CGRP depletion.

EXAMPLE 4

Cis-8-methyl-N-vanillyl-6-nonenamide in a concentration of 0.075% was incorporated into the inert cream vehicle of Example 1 and applied four times daily to the chest of a patient with painful postherpetic neuralgia who had been unable to tolerate the burning produced by earlier applications of capsaicin. The patient experienced no burning or stinging on application of the cis-8-methyl-N-vanillyl-6-nonenamide cream and within 2 weeks noted marked reduction of his pain.

EXAMPLE 5

Using the same inert cream vehicle of Examples 1 and 4, vehicle cream containing 0.75% capsaicin and an identical vehicle cream containing 0.75% cis-8-methyl-N-vanillyl -6-nonenamide were applied to the right and left feet and legs respectively of a patient with symmetrical diabetic neuropathy. Both creams were applied three times daily for 4 weeks. At the end of this 4 week treatment period, the left leg which had been treated with the cis-8-methyl-N-vanillyl6-nonenamide cream was markedly less painful than prior to treatment, while the right leg which had been treated with capsaicin cream demonstrated moderate reduction in pain. The patient complained of slight stinging and burning for the first 5 days on application of capsaicin cream, but no stinging or burning at any time during application of the cis-8-methyl-N-vanillyl-6-nonenamide.

While the foregoing is a description of the preferred embodiments of the instant invention it will be readily apparent to those skilled in the art that various modifications may be made therein without departing from the true scope and spirit of the invention as set forth in the appended claims.

I claim:

1. A composition comprising cis-8-methyl-N-vanillyl-6nonenamide in an amount of about 0.001% to about 1.0% by weight and a pharmaceutically acceptable vehicle, said composition for use in the treatment of painful or allergic disorders, said composition being comparable in efficacy to compositions containing capsaicin but with significantly less local adverse effects normally associated with capsaicin.

2. The composition of claim 1 wherein said composition is suitable for application to the skin.

3. The composition of claim 2 wherein said vehicle is selected from the group consisting of a lotion, a solution, a cream, an ointment, a gel, or a paste.

4. The composition of claim 1 wherein said composition is suitable for application to mucous membranes.

5. The composition of claim 4 wherein said vehicle is selected from the group consisting of solutions, suspensions, suppositories, and plasticized formulations.

6. The composition of claim 1 wherein said composition is suitable for injection.

7. The composition of claims 1, 3, 5, or 6 cis-8-methyl-N-vanillyl-6-nonenamide is present in the amount of about 0.005% to about 0.25% by weight.

8. A method of treating painful or allergic disorders comprising treatment with an effective amount of a composition containing cis-8-methyl-N-vanillyl-6-nonenamide in an amount of about 0.001% to about 1.0% by weight in a pharmaceutically acceptable vehicle, said composition being comparable in efficacy to compositions containing capsaicin but with significantly less local adverse effects normally associated with capsaicin.

9. The method of claim 8 wherein said method of treatment is selected from the group consisting of application of skin, application to mucous membrane and injection.

10. The method of claim 8 wherein said method cis-8-methyl-N-vanillyl-6-nonenamide is present in the amount of about 0.005–0.25% by weight.

11. A composition suitable for oral administration, comprising a pharmaceutically acceptable vehicle in the form of capsules, tablets, liquid solutions or suspensions and containing cis-8-methyl-N-vanillyl-6-nonenamide present in an amount of about 0.1–100.0 mg. per capsule, tablet, or 5 ml. portion of liquid, said composition being comparable in efficacy to compositions containing capsaicin but with significantly less local adverse effects normally associated with capsaicin.

12. The composition of claim 11 wherein cis-8-methyl-N-vanillyl-6-nonenamide is present in the amount of amount of 0.5–50.0 mg per capsule, tablet, or 5 ml portion of liquid.

13. A method of treating painful or allergic disorders by oral administration and comprising treatment with an effective amount of a composition containing cis-8-methyl-N-vanillyl-6-nonenamide in an amount of about 0.1–100.0 mg. per dose or 5 ml. portion of liquid in a pharmaceutically acceptable vehicle, said composition being comparable in efficacy to compositions containing capsaicin but with significantly less local adverse effects normally associated with capsaicin.

14. The method of claim 13 wherein said cis-8-methyl-N-vanillyl-6-nonenamide is present in the amount of about 0.5–50.0 mg per dose.

* * * * *